(12) United States Patent
Hoffmann et al.

(10) Patent No.: US 11,948,332 B2
(45) Date of Patent: Apr. 2, 2024

(54) METHOD AND AN APPARATUS FOR DETERMINING A GAZE POINT ON A THREE-DIMENSIONAL OBJECT

(71) Applicant: APPLE INC., Cupertino, CA (US)

(72) Inventors: Jan Hoffmann, Berlin (DE); Tom Sengelaub, Berlin (DE); Denis Williams, Berlin (DE)

(73) Assignee: APPLE INC., Cupertino, CA (US)

(*) Notice: Subject to any disclaimer, the term of this patent is extended or adjusted under 35 U.S.C. 154(b) by 0 days.

(21) Appl. No.: 18/111,099

(22) Filed: Feb. 17, 2023

(65) Prior Publication Data
US 2023/0206494 A1 Jun. 29, 2023

Related U.S. Application Data

(63) Continuation of application No. 16/878,932, filed on May 20, 2020, now Pat. No. 11,676,302, which is a (Continued)

(30) Foreign Application Priority Data

Sep. 17, 2012 (EP) ..................... 12184725

(51) Int. Cl.
*G06K 9/00* (2022.01)
*A61B 3/113* (2006.01)
(Continued)

(52) U.S. Cl.
CPC ............... *G06T 7/75* (2017.01); *A61B 3/113* (2013.01); *G06V 40/19* (2022.01);
(Continued)

(58) Field of Classification Search
None
See application file for complete search history.

(56) References Cited

U.S. PATENT DOCUMENTS 6,130,957 A 10/2000 Horikoshi
8,885,882 B1 11/2014 Mn
(Continued)

FOREIGN PATENT DOCUMENTS

CN 101943982 A 1/2011
JP 2005-071041 A 11/2005
(Continued)

OTHER PUBLICATIONS

Munn, Susan M., et al. "3D Point-of-Regard, Position and Head Orientation from a Portable Monocular Video-Based Eye Tracker" Visual Perception Laboratory, Carlson enter for Imaging Science, Rochester Institution of Technology, Rochester, NY, Mar. 26-28, 2008, pp. 180-188.
(Continued)

*Primary Examiner* — Wei Wen Yang
(74) *Attorney, Agent, or Firm* — Fernando & Partners, LLP

(57) ABSTRACT

A system for determining the gaze endpoint of a subject, the system comprising: a eye tracking unit adapted to determine the gaze direction of one or more eyes of the subject; a head tracking unit adapted to determine the position comprising location and orientation of the eye tracker with respect to a reference coordinate system; a 3D Structure representation unit, that uses the 3D structure and position of objects of the scene in the reference coordinate system to provide a 3D structure representation of the scene; based on the gaze direction, the eye tracker position and the 3D structure representation, calculating the gaze endpoint on an object of the 3D structure representation of the scene or determining the object itself.

20 Claims, 4 Drawing Sheets

Related U.S. Application Data continuation of application No. 16/290,934, filed on Mar. 3, 2019, now Pat. No. 10,699,439, which is a continuation of application No. 14/428,608, filed as application No. PCT/EP2013/069236 on Sep. 17, 2013, now Pat. No. 10,223,808.

(51) Int. Cl.
  *G06T 7/73* (2017.01)
  *G06V 40/19* (2022.01)

(52) U.S. Cl.
  CPC ............... *G06T 2200/04* (2013.01); *G06T 2207/10028* (2013.01); *G06T 2207/20076* (2013.01); *G06T 2207/30201* (2013.01)

(56) References Cited

U.S. PATENT DOCUMENTS

| | | | |
|---|---|---|---|
| 2011/0006978 A1 | 1/2011 | Yuan | |
| 2011/0019874 A1* | 1/2011 | Jarvenpaa | A61B 3/113 382/103 |
| 2012/0051597 A1 | 3/2012 | Fogt | |
| 2012/0169887 A1 | 7/2012 | Zhu et al. | |
| 2014/0181106 A1 | 6/2014 | Horowitz | |

FOREIGN PATENT DOCUMENTS

| | | |
|---|---|---|
| JP | 2006-119297 | 5/2006 |
| JP | 2007-286995 | 11/2007 |
| JP | 2012-050837 A | 3/2012 |
| JP | 2012-128661 A | 7/2012 |
| JP | 2012-515579 A | 7/2012 |
| JP | 2012-170546 A | 9/2012 |
| KR | 20080010041 A | 1/2008 |
| WO | 2011003303 A1 | 1/2011 |

OTHER PUBLICATIONS

Takemura, Kentaro et al., "Estimating 3D Point-of-Regard and Visualizing Gaze Trajectories under Natural Head Movements", Graduate School of Information Science,Nara Institute of Science and Technology, Japan, Mar. 22-24, 2010, pp. 157-160.

Office Action for Chinese Appl. No. 201380048140 dated Sep. 28, 2017.

Office Action for Japanese Appl. No. 2015-531598 dated Apr. 20, 2017.

Li Sun, et al., "Eyewatchme-3D Hand and Object Tracking for Inside Out Activity Analysis", Computer Vision and Pattern Recognition Workshops, Jun. 20, 2009, p. 9-16.

Office Action for Japanese Appl. No. 201380048140 dated Aug. 5, 2019.

* cited by examiner

METHOD AND AN APPARATUS FOR DETERMINING A GAZE POINT ON A THREE-DIMENSIONAL OBJECT

CROSS-REFERENCE TO RELATED APPLICATIONS

This application is a continuation of U.S. patent application Ser. No. 16/878,932, filed on May 20, 2020, which is a continuation of U.S. patent application Ser. No. 16/290,934, filed on Mar. 3, 2019, which is a continuation of U.S. patent application Ser. No. 14/428,608, filed on Mar. 16, 2015, which is the national phase entry of Intl. App. No. PCT/EP2013/069236, filed on Sep. 17, 2013, which claims priority to European Patent App. No. 12184725.5, filed on Sep. 17, 2012, all of which are hereby incorporated by reference in their entireties.

FIELD OF THE INVENTION

The present invention relates to a method and an apparatus for gaze endpoint determination, in particular for determining a gaze endpoint of a subject on a three-dimensional object in space.

BACKGROUND OF THE INVENTION

There are existing solutions to the problem of finding the point or the object or more specific the part of an object's surface that a (possibly moving) person gazes at. Such solutions are described below and can be split into separate parts.

At first the gaze direction of the person (or a representation thereof like a pupil/CR combination, cornea center and pupil/limbus etc.) is to be found.

For determining the gaze direction eye trackers can be used. Eye Trackers observe features of the eye like the pupil, the limbus, blood vessels on the sclera, the eyeball or reflections of light sources (corneal reflections) in order to calculate the direction of the gaze.

This gaze direction is then mapped to an image of the scene captured by a head-mounted scene camera or a scene camera at any fixed location. The head-mounted scene camera is fixed with respect to the head, and therefore such a mapping can be performed, once a corresponding calibration has been executed. For performing the calibration a user may have to gaze at several defined points in the scene image captured by the head-mounted camera. By using the correspondingly detected gaze directions the calibration can be performed resulting in a transformation which maps a gaze direction to a corresponding point in the scene image. In this approach any kind of eye tracker can be used if it allows mapping the gaze direction into images of a head-mounted scene camera.

This approach enables the determination of a gaze point in the scene image as taken by the head-mounted scene camera.

As a next step it can be of interest to map the gaze point in the scene image as captured by the head-mounted scene camera, which can change due to the movement of the subject, to a point in a (stable) reference image which does not move and which corresponds to a "real world" object or an image thereof. The reference image thereby typically is taken from a different camera position than the scene image taken by the head-mounted scene camera, because the scene camera may move together with the head of the user.

For such a case where the head moves, there are known approaches for determining the gaze point in a reference image which does not move based on the detection of the gaze direction with respect to a certain scene image as taken by the head-mounted scene camera even after the head has moved.

One possible approach of determining the point gazed at is to intersect the gaze direction with a virtual scene plane defined relative to the eye tracker. WO 2010/083853 A1 discloses to use active IR markers for that purpose, which are fixed at certain locations, e.g. attached to a bookshelf. The locations of these markers are first detected with respect to a "test scene" which acts as a "reference" image obtained by the head-mounted camera, by use of two orthogonal IR line detectors which detect the two orthogonal angles by detecting the maximum intensity of the two line sensors. The detected angles of an IR source correspond to its location in the reference image. Then the angles of the markers are detected for a later detected scene taken by the head-mounted camera from a different position, thereby detecting the location of the IR sources in the later scene image. Then there is determined the "perspective projection", which is the mapping that transforms the locations of the IR sources as detected in an image taken later (a scene image), when the head-mounted camera is at a different location, to the locations of the IR light sources in the test image (or reference image). With this transformation a gaze point as determined later for the scene image can also be transformed into the corresponding (actual) gaze point in the test image.

The mapping of the gaze point from the actual "scene image" to a stable reference image which is time invariant becomes possible by defining the plane on which the gaze point is mapped in relation to scene stable markers instead of to the eye tracker (ET). This way the plane of the reference image becomes stable over time and gazes of other participants can also be mapped onto it so that the gaze point information can be aggregated over time as well as over participants like it could only be done before with eye trackers located at a fixed position.

For that purpose the prior art as disclosed in WO 2010/083853 A1 uses IR sources as artificial markers the locations of which can be detected by orthogonal IR line detectors to detect the angles of maximum emission.

The usage of using IR sources as markers for determining the transform of the gaze point from a scene image to a reference image is complicated and inconvenient.

In the European Patent application no. EP11158922.2 titled Method and Apparatus for Gaze Point Mapping and filed by SensoMotoric Instruments Gesellschaft far innovative Sensorik mbH which is incorporated herein by reference there is described a different approach. In this approach there is provided an apparatus for mapping a gaze point of a subject on a scene image to a gaze point in a reference image, wherein said scene image and said reference image have been taken by a camera from a different position, said apparatus comprising:

A module for executing a feature detection algorithm on said reference image to identify a plurality of characteristic features and their locations in said reference image;

a module for executing said feature detection algorithm on said scene image to re-identify said plurality of characteristic features and their locations in said scene image;

a module for determining a point transfer mapping that transforms point positions between said scene image and said reference image based on the locations of said plurality of characteristic features detected in said reference image and said scene image;

a module for using said point transfer mapping to map a gaze point which has been determined in said scene image to its corresponding point in said reference image.

This enables the implementation of gaze point mapping which does not need any artificial IR sources and IR detectors. It can operate on normal and unamended images of natural scenes taken by normal CCD-cameras operating in the visible frequency range. For a detailed description of this approach reference is made to European Patent application no. EP11158922.2.

But even with this approach it is only possible to map a gaze of a moving subject to a certain predefined static plane, however, the determination of a gaze endpoint at any arbitrary object in 3D space is not possible.

It is therefore an object of the invention to provide an approach which can determine the gaze endpoint at any arbitrary three-dimensional object in 3D-space.

SUMMARY OF THE INVENTION

According to one embodiment there is provided a system for determining the gaze endpoint of a subject, the system comprising:
- an eye tracking unit adapted to determine the gaze direction of one or more eyes of the subject;
- a head tracking unit adapted to determine the position comprising location and orientation of the head and/or the eye tracking unit with respect to a reference coordinate system;
- a 3D scene structure representation unit, that represents a real-world scene and objects contained in the scene by representing the objects of the real-world scene through their 3D position and/or their 3D-structure through coordinates in the reference coordinate system to thereby provide a 3D structure representation of the scene;
- a calculating unit for calculating the gaze endpoint based on the gaze direction, the eye tracker position and the 3D scene structure representation, and/or for determining the object in the 3D scene the subject is gazing at based on the gaze direction, the eye tracker position and the 3D scene structure representation By using a 3D representation, an eye tracker and a head tracker there can be determined not only a gaze point on a 2D plane but also an object the subject is gazing at and/or the gaze endpoint in 3D.

According to one embodiment the system comprises a module for calculating the gaze endpoint on an object of the 3D structure representation of the scene, wherein said gaze endpoint is calculated based on the intersection of the gaze direction with an object in the 3D structure scene representation.

The intersection of gaze direction with the 3D representation gives a geometrical approach for calculating the location where the gaze "hits" or intersects the 3D structure and therefore delivers the real gaze endpoint. Thereby a real gaze endpoint on a 3D object in the scene can be determined.

According to one embodiment the system comprises a module for calculating the gaze endpoint based on the intersection of the gaze directions of the two eyes of the subject, and/or a module for determining the object the subject is gazing at based on the calculated gaze endpoint and the 3D position and/or 3D structure of the objects of the real world scene.

By using the vergence to calculate the intersection of the gaze direction of the eyes of the subject there can be determined the gaze endpoint. This gaze endpoint can then be used to determine the object the user is gazing at.

According to one embodiment the object being gazed at is determined as the object the subject is gazing at by choosing the object whose 3D position and/or structure is closest to the calculated gaze endpoint, According to one embodiment said eye tracking unit which is adapted to determining the gaze direction of the said one or more eyes of said subject is adapted to determine a probability distribution of said gaze direction of said one or more eyes, and wherein said calculating unit for determining the object being gazed at determines for one or more objects the probability of said objects being gazed at based on a probability distribution of gaze endpoints.

In this manner there can be determined a probability distribution which indicates the probability that the subject gazes at a certain object.

According to one embodiment the system further comprises:
- a scene camera adapted to acquire one or more images of the scene from an arbitrary viewpoint;
- a module for mapping a 3D gaze endpoint onto the image plane of the scene image taken by the scene camera.

In this way not only the 3D gaze endpoint on the 3D structure is determined, but there can be determined the corresponding location on any scene image as taken by a scene camera. This allows the determination of the gaze point in a scene image taken by a camera from an arbitrary point of view, in other words form an arbitrary location.

According to one embodiment the position of the scene camera is known or determined by some position determination or object tracking mechanism and the mapping is performed by performing a projection of the 3D gaze endpoint onto an image of said scene camera.

This is a way of deriving from the 3D gaze endpoint the corresponding point in a scene image taken by a camera at an arbitrary location.

According to one embodiment the system further comprises:
- A module for generating a scene image as seen from an arbitrary viewpoint based on the 3D structure representation;
- a module for mapping a 3D gaze endpoint onto the image plane of the image generated by said scene image generating module, wherein the mapping is performed by performing a projection of the 3D gaze endpoint onto the image plane of said scene image generated by said scene image generating module.

In this manner an arbitrary scene image can be generated not by taking an image using a scene camera but instead by generating it based on the 3D structure representation. In this scene image then the gaze endpoint or the object being gazed at can be indicated or visualized by projecting the gaze endpoint onto the scene image or by e.g. highlighting the object which has been determined as the object of the 3D structure being gazed at in the scene image.

According to one embodiment said eye tracker is a head-mounted eye tracker; and/or said scene camera is a head-mounted scene camera.

Head-mounted eye tracker and head-mounted scene cameras are convenient implementations of these devices. Moreover, if the eye tracker is head-mounted, then the head tracker automatically also delivers the position/orientation of the eye tracker. The same is true for the scene camera. Using the position (location and orientation) of the head as determined by the head tracker one can determine based on the gaze direction as determined by the head-mounted eye tracker in the coordinate system of the eye tracker a corresponding gaze direction in the reference coordinate system of the head tracker. This can be done by a simple transformation which transforms the gaze direction from the eye tracker's coordinate system into the coordinate system of the head tracker using the head location and orientation as determined by the head tracker. The position delivered by the head tracker automatically also delivers the position of the eye tracker through the given setup in which the eye tracker is fixed to the head and has a defined spatial relationship with the head, e.g. by the mounting frame through which it is mounted on the head.

According to one embodiment said 3D Structure representation unit comprises a 3D scene structure detection unit that is adapted to determine the 3D structure and position of objects of the scene or their geometric surface structure in the reference coordinate system to obtain a 3D structure representation of the real-world scene.

In this way the 3D structure or at least the relevant, visible part of it can be directly obtained from the scene by using the structure detection unit.

According to one embodiment said 3D structure detection unit comprises one of the following:
- a laser scanner, possibly combined with a camera;
- an optical scanner together with a light source emitting structured light;
- a stereo camera system;
- an ultrasound detector;
- any mechanical detection implementation.

These are convenient implementations of the 3D structure detection unit.

According to one embodiment the system comprises one or more of the following:
- 3D gaze endpoints are mapped to one or more scene images taken by a plurality of different scene cameras and/or to scene images taken from different viewpoints;
- 3D gaze endpoints are mapped for a plurality of different subjects to the same scene image;
- 3D gaze endpoints are mapped or aggregated over time to the same scene image, possibly for different subjects.

This takes advantage of the flexibility of the approach by mapping the gaze endpoints for different users and/or for different scene cameras at different locations. The recording of gaze endpoints and the mapping to one or more possibly different scene images can be performed over time, possibly even for different subjects, thereby obtaining a representation of the gaze data in a desired way.

According to one embodiment the mapped 3D gaze endpoints over time are visualized in the scene image by visualizing the 3D gaze endpoints together with the corresponding frequency of views or accumulated viewing time, possibly distinguished according to different subjects.

This allows a visualization of the measured gaze endpoints and their mapped scene locations.

According to one embodiment said visualization uses one or more of:
- A heat map;
- A focus map;
- The center of gravity of gaze;
- An automatic contour of viewing time.

These are suitable implementations for the visualization.

According to one embodiment said 3D Structure Detector repeatedly determines said 3D structure to enable a real-time gaze point detection using said eye tracker and said head tracker even if said 3D scene is not static, or said 3D scene Structure Detector initially determines said 3D structure and an object tracker tracks the movement of one or more objects in the scene to thereby enable a gaze point determination over time using the tracked objects and the tracked gaze direction over time.

In this way an online measurement can be implemented even for non-static scenes.

According to one embodiment said 3D Structure detection unit comprises one or more scene cameras and a computation unit for calculating said 3D structure based on said one or more cameras' images.

In this way the 3D-structure detection unit can be implemented without specific hardware except a scene camera and a computation unit. The scene camera(s) according to one embodiment may be the same scene camera as is used for taking the scene image into which later the gaze endpoint is to be mapped According to one embodiment said computation unit uses a visual SLAM (visual Simultaneous Localization and Mapping) algorithm for calculating said 3D structure and/or the position of the scene camera.

This is a suitable implementation of a 3D structure detection unit by a scene camera and a computation unit.

According to one embodiment the system comprises:
- a display unit for displaying gaze data from one or more person with a visualization of statistic data on the reference model, wherein said visualization comprises:
- a visualization based on a projection onto the surface of objects;
- a visualization based on a fly-through visualization of the 3D structure.

These are suitable approaches for implementing visualizations of the measured gaze endpoints.

According to one embodiment the images of the one or more scene cameras are combined to one or more bigger images such as a panorama or a multiperspective image to be used as scene image or images, and/or wherein said 3D structure representation unit uses the 3D structure and position of objects of the scene in the reference coordinate system to provide a 3D structure representation of the scene which has been determined in advance.

These are other suitable approaches for implementing visualizations of the measured gaze endpoints.

Using a 3D structure representation unit instead of a structure determination unit makes it possible to use 3D data which has been determined in advance.

DETAILED DESCRIPTION

Figure 1A:
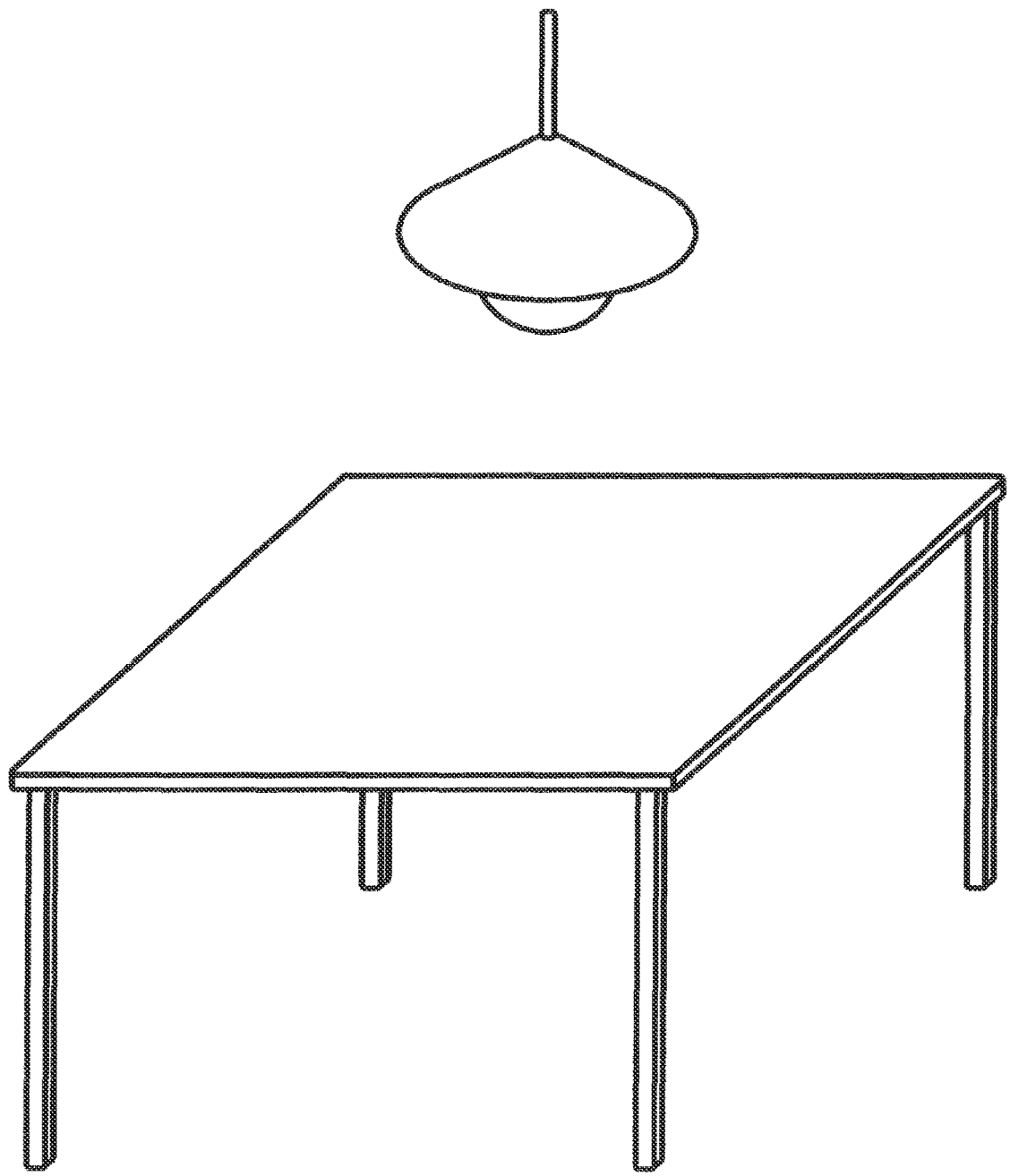
FIGS. 1A and 1B schematically illustrate an object representation according to an embodiment of the invention.

In the following there will be described embodiments of the invention.

According to one embodiment there is determined a determination of a gaze endpoint and in one embodiment also a mapping of the gaze endpoint not just for planes but for general objects in 3D-space. Moreover, according to one embodiment it can be determine which object in 3D-space a subject is gazing at.

According to one embodiment for that purpose there is used a 3D-structure detector, an object tracker for tracking the head of the subject and its orientation (a "head tracker") and an eye tracker. By tracking the head movement using the head tracker and the gaze direction of the eye of the subject using the eye tracker there can be obtained the gaze direction of the subject in the 3D-space. This gaze direction can then by projected or intersected with the 3D-model of the "world" which is obtained from the 3D-structure detector and viewed by the subject. Thereby the point in the 3D-model to which the gaze of the subject is directed and where it is "hitting an object" of the 3D structure can be determined. In this way the "gaze endpoint" and thereby also the object at which the subject gazes at can be determined.

According to a further embodiment the gaze endpoint is determined based on the vergence of the eyes. In this embodiment the eyetracker detects the gaze direction of the two eyes of the subject. When the subject looks at a certain object, then the gaze directions of the two eyes are not parallel but they are directed to the same object which means that they intersect at the point of regard the subject is looking at. This means that if the gaze directions of the two eyes are obtained by the eyetracker, the calculation of the intersection of the thus obtained gaze directions in 3D-space actually provides the point of regard in 3D space.

It may happen that the two gaze directions which are determined for the two eyes of the subject do in fact not intersect at a certain point in space. The reason may be that there is indeed no intersection, which means that the two gaze directions indeed do not converge and intersect at the same point in space, or the lack of an intersection point may be caused by a measurement error. Nevertheless, in both cases there may still be determined a gaze endpoint based on an intersection, e.g. by choosing the point which lies halfway on the distance vector between the two gaze directions, in other words the point in 3D space which lies closest to the two gaze directions.

By using the thus determined gaze endpoint and a representation of objects in 3D space it can then be determined which object the subject is gazing at. This representation can be e.g. a full 3D structure representation of the objects which are according to one embodiment obtained by a structure generation unit. The 3D structure representation of the objects define the structure of the objects (e.g. by their boundaries). If the gaze endpoint determination is exact and without error, then it typically will lie on the surface of an object of the 3D structure, and this is then the point which is determined as the point the subject is gazing at. Once the gaze endpoint has been determined, from the 3D structure representation there also follows the object the gaze endpoint is lying on, and thereby the object the user is gazing at.

There may occur situations where the gaze endpoint does not lie on an object. This may be due to different reasons, one being e.g. that the gaze endpoint determined by vergence is not fully correct and exact, and then the thus determined gaze endpoint may lie somewhere in empty space where no object is located. According to one embodiment, however, even in such a situation there may be determined the object being gazed at, e.g. by determining the object which is closest to the gaze endpoint. This object may then be chosen as the one for which it has been determined that the subject is gazing at it.

Another approach for determining the object gazed at by the subject is checking if both gaze vectors intersect with the volume of the object. In such a case, the object with which both gaze vectors intersect is determined to be the object at which the user is gazing.

According to one embodiment the gaze directions of the two eyes may be used to determine a "combined" gaze direction. This can e.g. be done by first calculating the gaze endpoint based on the vergence as the intersection of the gaze direction of the two eyes. The resulting gaze endpoint then can be used to determine a gaze direction which is based on the gaze direction of the two eyes, in other words a "combined gaze direction". This can according to one embodiment be done by choosing as gaze direction a vector which originates e.g. between the eyes of the subject and passes through gaze endpoint which has been determined based on the intersection. The resulting combined gaze direction can then be used for calculating its intersection with an object of the 3D structure to determine the object being gazed at.

According to one embodiment the eye tracking unit which is adapted to determine the gaze direction of the one or more eyes of the subject is adapted to determine a probability distribution of the gaze direction of the eye or the eyes. This probability distribution may indicate for a determined gaze direction a likelihood of being correct. It can e.g. be obtained based on the (known or estimated) accuracy or "error distribution" of the eye tracker. This accuracy gives for a measurement value (i.e. the gaze direction) the probability that it is correct and—in form of a probability distribution—indicates for different values the likelihood that they are the correct measurement value. Using such a probability distribution one can—for the points in 3D space—indicate the probability that they are lying on the measured gaze direction.

This probability distribution according to one embodiment is used to determine for a plurality of objects their corresponding probability of being gazed at. The probability distribution of the measured gaze direction corresponds to a probability distribution of different gaze endpoints. The probability distribution thereby may e.g. reflect the error distribution of the measured gaze direction. E. g. if there is measured a certain gaze direction, then the error distribution indicates the different likelihoods of different gaze directions being correct due to some measurement error (as indicated by the error distribution or "probability distribution"). Because for these different gaze directions there are resulting different gaze endpoints one can based on the different gaze endpoints and their corresponding probabilities obtain the respective probabilities of the corresponding objects being gazed at. This can e.g. be done by integrating the gaze probabilities of the individual points which belong to the surface of an object over the whole surface of this object. In this manner there is obtained a gaze endpoint probability distribution based on the gaze direction probability distribution, and this is used to determine a probability distribution which indicates for the various objects in 3D space their probability of being gazed at. In this embodiment the "calculating unit for determining the object being gazed at" therefore actually determines the probability of an object being gazed as an implementation of the "determination of the object being gazed at", in other words this is a specific embodiment of a calculating unit for determining the object being gazed at.

According to one embodiment the probability distribution of the gaze direction can be used also for the gaze directions determined for the two eyes of the subject. In this embodiment each of the two gaze directions has its own probability distribution which reflects the likelihood of a certain gaze direction being correct. Based thereon there can then for each point in 3D space be calculated the likelihood that this is the gaze endpoint as the intersection of the two gaze directions. In other words, this results then in a probability distribution indication which for a point in 3D space indicates its probability of being the gaze endpoint. This probability distribution according to one embodiment is used to determine the probability of a certain object being gazed at; it follows directly from the probability distribution of the gaze endpoints.

According to one embodiment, as mentioned before, the probability distribution of the gaze direction reflects the "accuracy" or "error" of the measurement of the gaze direction. It may be determined by measuring the error distribution or it may just be estimated. According to a further embodiment not only the gaze direction is determined with a certain error being reflected by a probability distribution but also the position of the objects in 3D space. For each object in 3D space there is according to one embodiment an uncertainty of its accuracy which is reflected by a probability distribution with respect to the location of the object. This probability distribution can then be combined with the probability distribution of the gaze direction (s) or the probability distribution of the gaze endpoints to obtain a combined probability for a certain object being gazed at which reflects both uncertainties.

According to a further embodiment the objects need not to be represented by a full 3D representation of their shape, location and orientation. Instead, each object may just be represented by one representative point in space which represents the location of the object in the 3D space. This representative point may e.g. be the center of gravity of the 3D object. Alternatively it may be any point, e.g. a user defined or user selected point, which represents the location of the object in 3D space may be chosen as representative point in 3D space which represents the location of the object. In this way the location of multiple objects may be represented in 3D space. Based on the gaze endpoint determined by vergence there can then be determined the point which represents an object which is most close to the gaze endpoint. In this way it may be determined that the subject is gazing at this object.

The object may also not just be represented by a single point, it may be represented by some representative 3D representation which has some extension in two or 3 dimensions, e.g. by a plane area, or by a 3D shape like a sphere which has a representative point as a center. One can use any space tessellation based on the scene objects here which can be used to represent an object.

Figure 1B:
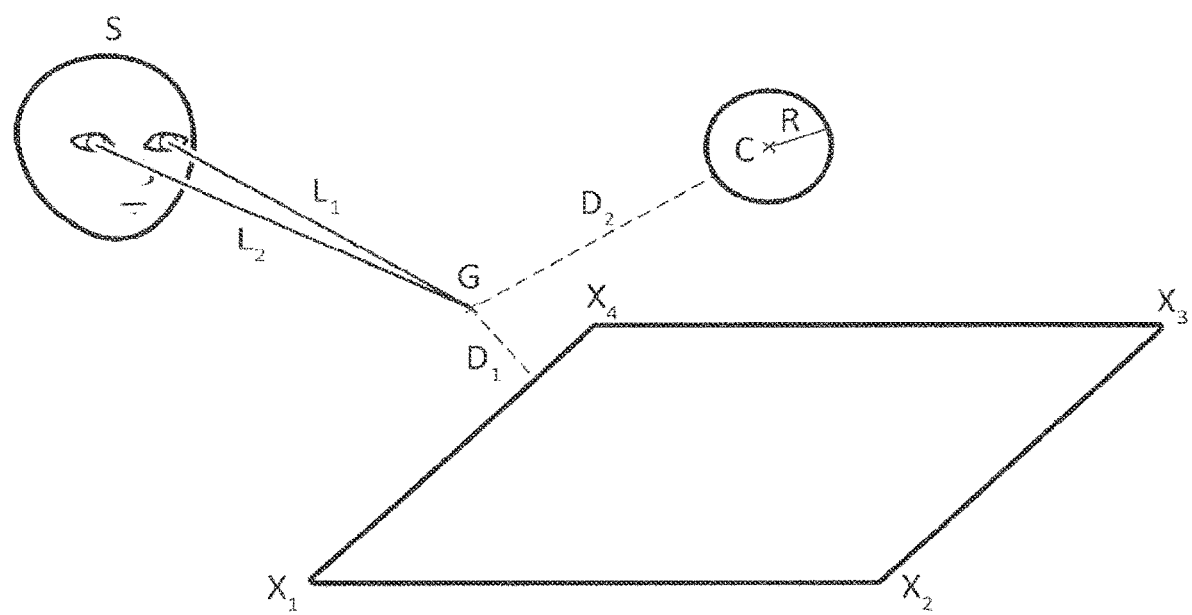

This is now illustrated in connection with FIGS. 1A and 1B. FIG. 1A shows an example of a 3D real world scene. It includes a table and a lamp hanging from the ceiling as real world objects. The 3D representation of these objects is illustrated in FIG. 1B. The lamp is represented by a sphere having a center C in 3D space and a radius R.

The table is represented by a rectangle with its corners X1, X2, X3 and X4. The coordinates of X1 to X4 and C may be determined by some measurement to determine the 3D coordinates. The radius R may be chosen such that it somehow resembles the shape of the "real lamp".

This then results in a configuration as shown in FIG. 1B with two objects whose 3D location is represented by some representation in 3D space. Also shown is the head of the subject S. The position and orientation of the head in 3D space may be determined by some object tracker (not shown), the gaze directions are obtained by some eyetracker, e.g. a head-mounted eyetracker (not shown). Using the gaze directions obtained by the eye tracker and the position and orientation from the head tracker (in its own coordinate system) one can then determine the gaze directions L1 and L2 in 3D space. This will later be explained in even more detail.

Then the gaze direction intersection point G is determined as the point of regard based on the vergence. As can be seen from FIG. 1A it does not lie on one of the object representations, neither on the lamp nor on the table. Then there is determined the distance from the gaze point G to the table and the lamp. It can be seen that the distance to the table D1 is closer than to the lamp, and therefore the system then can conclude that the subject gazes at the table.

In this manner the system can determine the object a user is gazing at in 3D space.

According to another embodiment the 3D representation of the objects uses a more accurate representation with higher granularity, e.g. a mesh representing the surface of the objects in 3D. In principle, however, the system then may operate in the same manner. If the gaze point is determined more accurately and lies on or near the surface of the 3D object representation, then the system may not only determine the object the subject is gazing at but even the location on the object the user is gazing at.

Now another embodiment will be described in somewhat more detail. In this embodiment the objects are represented by a 3D structure representation, and the object the subject is gazing at is determined based on the intersection of the gaze direction with the 3D object representation rather than based on vergence.

In other words, with this approach based on a gaze direction which is determined and intersected with a 3D structure representing the "real world" objects there can be determined a gaze endpoint on a 3D-object. According to one embodiment the thus determined gaze endpoint can be mapped to a corresponding location in any image of the scene. Moreover, in this way the problem of identifying the objects gazed at reduces to naming the objects/object parts, since the approach directly delivers the object the user gazes at because the gaze direction intersects with the object the user is gazing at.

According to one embodiment a system for mapping a gaze onto a 3D-object operates as follows.

A detector to measure 3D Scene Structure (3D detector) is used to determine the surface structure, position and orientation of all or all relevant (e.g. selected ones or objects larger than a minimum size) objects in the scene resulting in a reference model (a 3D structure or "model of the 3D structure" of the "real world"). This reference model is a representation of the "world" which the user gazes at. It consists of a representation of the objects of the "world", e.g. by a mesh.

It is e.g. represented in a "reference coordinate system". The reference coordinate system is time invariant and static, in contrary e.g. to the coordinate system of a head mounted eye tracker which moves together with the head of the subject.

The eye's position (the same applies to multiple eyes) can be measured at any time in relation to the 3D Detector and in extension to the detected scene objects by using a Head Tracker that relates the eye's position to the 3D detector position and/or the head tracker's position (and thereby gives also its position in the reference coordinate system). Preferably there is not only given the location but also the orientation of the head or a head-mounted eye tracker by the head tracker. Also preferably the head tracker coordinate system is time invariant as is the reference coordinate system of the 3D structure detection unit. In one embodiment both coordinate systems are identical, in another embodiment there may be a time invariant transformation which transforms the head tracker coordinate system to the reference coordinate system of the 3D structure detection unit or vice versa.

By combining the 3D detector and the Head Tracker with an Eye Tracker, that measures the gaze direction, the gaze intersection with surfaces of objects of the 3D structure can be calculated. The head-mounted eye tracker outputs the gaze direction in the coordinate system of the head/eye tracker. Since the head position and its orientation is known from the head tracker, the location and orientation of the eye tracker also is known due to the known setup of the eye tracker being head mounted. Using this information from the head tracker the gaze direction in the reference coordinate system (the system in which the 3D structure is represented) can be derived based on the gaze direction determined by the eye tracker in the eye tracker coordinate system by a simple transformation of the eye tracker coordinate system to the reference coordinate system. The transformation follows directly from the measured location and orientation of the head measured by the head tracker.

This gaze direction can then be intersected with the 3D structure representation of the scene to detect the 3D gaze endpoint on an object of the 3D structure. Thus there is provided a measurement device that measures the gaze endpoint of a person's (or a subject's) eye on 3D objects in the scene as well as parameters of the objects themselves.

This is a significantly novel approach for determining the gaze point. It is quite different from knowing the gaze point on images of the scene because in such a case objects have to be designated by hand for each image.

The approach extends over the previous approach of determining the gaze point on a real scene plane by now detecting a 3D gaze endpoint on a 3D structure detected by the 3D-structure detector. Because the previous approach using a scene plane operates only in a 2D space it does not cover points with parallax induced by object points off the plane, of which there are usually plenty in real scenes. Therefore the present approach also overcomes such parallax problems.

Once the gaze endpoint on a 3D object has been determined the gaze endpoint can also be mapped to any image of the scene taken from any arbitrary location by a camera. For that purpose the camera's parameters and its position relative to the scene are needed. They may be known by definition of the setup/calibration, or both can also be calculated out of the image itself given the scene structure, or they may be otherwise measured.

According to a further embodiment the scene image is not taken by a scene camera but instead is generated based on the 3D structure representation, e.g. by projecting the structure into the image plane of the (arbitrary) scene image. Then in this arbitrary scene image the object of the 3D structure which has been determined as the object being gazed may be highlighted, or the gaze endpoint of the subject may be visualized by projecting it from the 3D structure into the scene image.

According to one embodiment a user can name objects or even more detailed object parts of the 3D structure by hand. In this way objects may be "tagged" with a name so that a "hit" of the gaze on such a named object then results in the return of the corresponding object name. Assuming the objects are the same over time, this has to be done only once and the gaze on any object can be determined for all participants and for all times any of the participants observed the scene. This is because the true 3D model of the object can cope with all possible views which may be taken by a user.

For unnamed objects which are not manually tagged or labeled, the system in one embodiment may assign default names.

Figure 2:
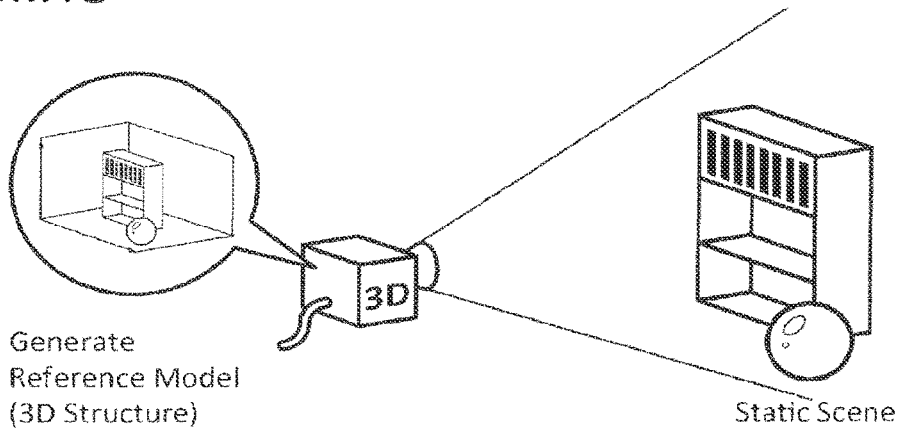
FIG. 2 schematically illustrates a gaze endpoint determination system according to an embodiment of the invention FIG. 3 schematically illustrates a gaze endpoint determination system according to a further embodiment of the invention.
Figure 2:
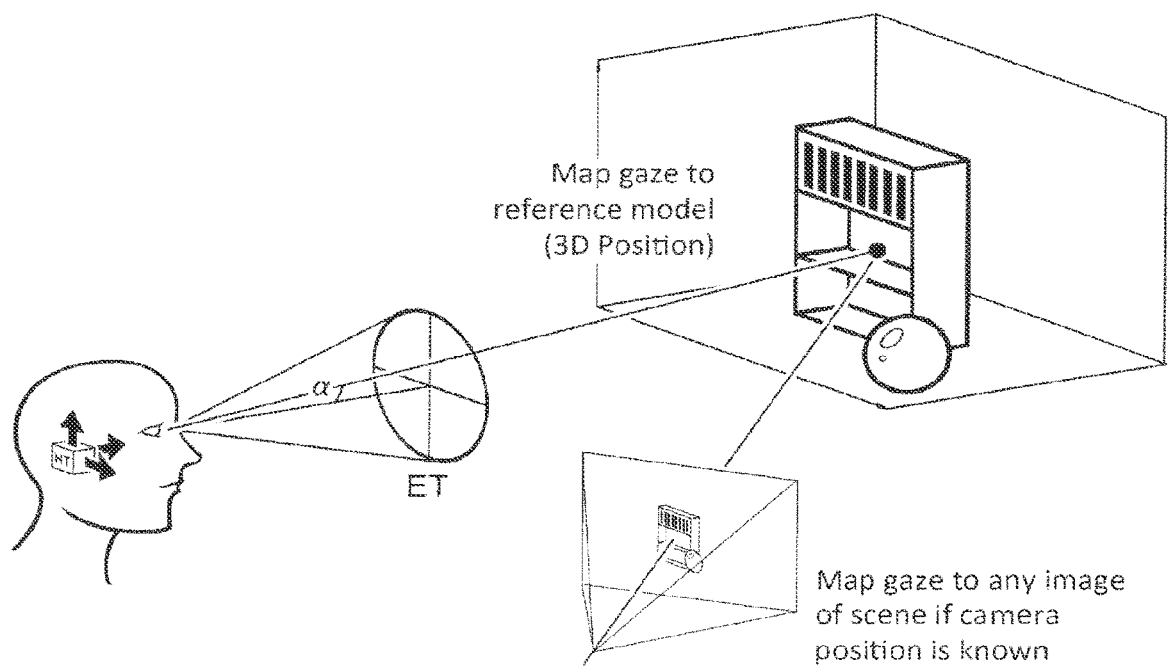

For static scenes according to one embodiment the reference model can be created offline. This is schematically illustrated in FIG. 2. The 3D-model/reference model is created "offline" using the 3D Structure Detector before the actual gaze measurement (this is illustrated as step a) in the upper part of FIG. 2. The 3D Structure Detector is not needed afterwards—the ET (eye tracker) and HT (head tracker) combination is then sufficient to determine the 3D gaze endpoint on the 3D structure which was determined in step a). This is illustrated in the upper part of step b) illustrated in FIG. 2 which shows the determination of the gaze endpoint on the 3D structure.

Then the mapping of the gaze endpoint onto the scene image taken by a scene camera can be performed. For that purpose any 3D projection method which maps the 3D structure to a 2D scene image using the position and parameters of the camera can be used. In this way the location where the gaze hits the 3D structure can be mapped onto the corresponding location at a scene image taken by a scene camera. This mapping process is schematically illustrated in the lower part of step b) in FIG. 2 which shows the mapping process (e.g. performed by using a 3D projection) of the 3D structure to a scene image.

Figure 3:
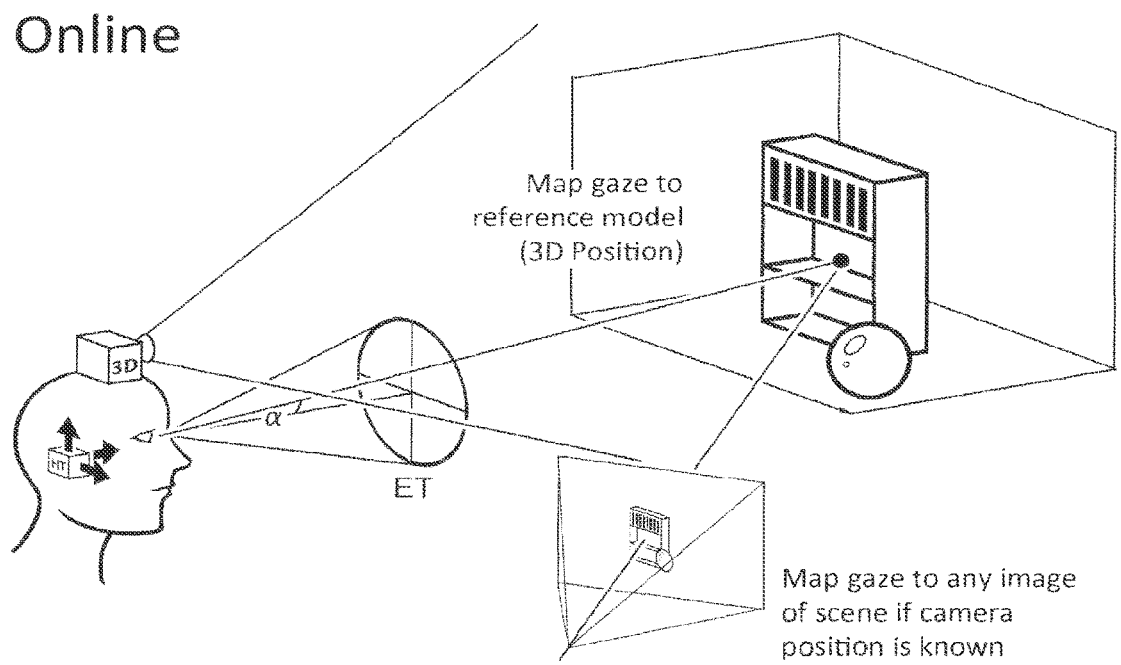

The above approach works for static scenes. If one is interested in dynamic scene content, according to one embodiment the 3D Structure Detector works in parallel to the ET and HT. This is schematically illustrated in FIG. 3 where the 3D structure is determined parallel to the determination of the gaze by the ET, the head position of the HT, and the gaze endpoint mapping to a scene image.

According to one embodiment the dynamic change of a scene can be taken into account by another mechanism. In this embodiment the 3D structure is determined only once, initially. However, the position and orientation of the relevant objects of the scene in the 3D space may be detected and tracked over time by one or more object trackers. The gaze direction also is tracked over time. Based on the thus obtained tracking data there can then be performed an offline processing which determines over time the intersection between the gaze direction and the moving objects and thereby determines the dynamic gaze endpoint.

Now there will be described a further embodiment with its components being described in somewhat more detail.

The components of this embodiment are gaze tracker, head tracker and 3D structure Detector. The gaze tracking can be realized by any of the conventional eye trackers. If a calibration is needed, the eye tracker is calibrated to a known plane in space so the gaze direction can be calculated from the gaze point on the plane.

As head trackers e.g. the following devices may be used:
A magnetic Head Tracker
Or an optical Head Tracker
Any kind of device that can measure the position and orientation of the ET (or the eye itself) with respect to the 3D Structure Detector (or the objects in the scene)

According to one embodiment there is used the scene camera in combination with the detected objects to calculate the scene camera's position and orientation. The camera may be the same scene camera as is used for taking the scene image into which later the gaze endpoint is to be mapped. For the purpose of determining the camera position there may be used a visual SLAM approach. A description of the visual SLAM approach can e.g. be found in Andrew J. Davison, "Real-Time Simultaneous Localisation and Mapping with a Single Camera", ICCV2003, or in Richard A. Newcombe and Andrew J. Davison, "Live Dense Reconstruction with a Single Moving Camera", CVPR2010.

According to another embodiment the camera position may just be measured, e.g. by internal sensors of the camera (e.g. a GPS sensor), or it may be determined in some other way (e.g. by an Inertial Measurement Unit or an object tracker).

According to one embodiment the ET position relative to the scene camera is known through the setup (both mounted on the same frame).

In order to determine the 3D structure several devices/approaches may be used.

Such measurement devices are e.g.
3D Scanners (Laser scanner, structured light scanner etc.)
Stereo camera system
Monocular camera system (e.g. visual SLAM)
Manual measurements With respect to manual measurements, for example, the plans for buildings are known in advance, e.g. from the construction plan, or the plans may have been derived by some "manual measurement". The 3D structure detection unit may then consist in just a device for "obtaining" or "reading" the stored 3D structure data which has been measured in advance, without performing an actual structure determination.

Instead of a 3D structure detection unit there may therefore be used a 3D structure representation unit which uses the 3D structure and position of objects of the scene in the reference coordinate system to provide a 3D structure representation of the scene. The measurement of the 3D structure may have been carried out in advance, and the structure representation unit then just uses the previously measured data to provide the 3D structure representation.

According to one embodiment there is used a camera (e.g. the scene camera) for static scenes to capture a video of the relevant scene part and calculate the scene structure by using a visual SLAM approach. Afterwards the approach allows also calculating the position of a camera taking an image of the scene from the image itself.

For dynamic scenes the structure can be measured online, which means that the 3D structure is repeatedly determined to take into account its dynamic changes. Otherwise a combination of offline (or initial) 3D structure detection and tracking of the object(s) of interest (e.g. with the help of an object tracker) can be used. For static scenes which do not change over time like supermarket shelves the structure can be measure once in advance.

The approach described before comes along with several advantages over existing approaches as shown below.

Objects are unique over the scene and by extension so is the gaze endpoint onto objects. Classification of gaze can be done per objects/object parts automatically if the classes of objects/object parts have been defined, irrespective of the position of the user and the scene image taken by the scene camera.

Gaze endpoints are decoupled from scene camera images. The gaze is mapped onto objects, not images of objects. For the ET with a scene camera the gaze can be remapped from the reference model objects to the image plane of the scene camera image. This is even true if the gaze point falls outside of the scene image.

Because the gaze endpoint is calculated in a geometrically correct way there is no parallax error in the gaze mapping, even if a non-parallax-free eye tracker is used.

It is possible to tell which object is actually gazed at in a scene where objects of interest are aligned behind each other such that multiple objects intersect the gaze path by using vergence. E.g. even if the gaze direction intersects with an object lying in front of another object, but if the vergence based intersection of the two gaze points lies on the object behind, then one may assume that the real gaze point is the object behind.

New visualizations of gaze data is possible:
aggregated over time and/or participants
on object surfaces (e.g. heat map)
3D visualizations of the gaze rays in space, of the objects in space, of objects textured with mapped gaze data (heat map, focus map, etc.)
automatic contour, center of gravity etc. of objects projected to a scene image
dynamic visualizations like fly throughs around the objects
aggregated gaze data on arbitrary scene images/on scene movies (of which the movie from a participant's scene camera is one special case)

In the following a further embodiment with its components will be described.

First of all the system comprises an eye tracker that provides the gaze direction of a person relative to the coordinate frame of the head. The gaze direction can also be defined indirectly as long it can be transformed to a head relative coordinate system.

Furthermore the system comprises a Head Tracker that detects the head or the eye tracker's coordinate system's location and orientation relative to a scene coordinate system. This can e.g. be done using sensors. In some cases these sensors detect their own position relative to the scene, then the sensor would need to be head mounted. However, any head tracking device may be used.

Furthermore the system comprises a 3D Structure Detector that measures the three dimensional surface structure of objects. The structure is made up out of the location, orientation and neighborhood of surface parts (points, patches, planes, or similar features used for describing 3D structure). The detector may also measure appearance of the objects.

Optionally the system also comprises a scene camera (possibly combined with a position detecting device so its position and orientation is known) that makes reference images of the scene.

Using these components there can be determined the gaze point on a 3D structure. Moreover, using the scene image and the scene camera's position there can be performed a mapping of the 3D gaze point onto the scene image.

Such a mapping can be performed onto any scene image given that the camera position of the camera which takes the scene image is known, e.g. by using 3D projection of the 3D-gaze point onto the scene image.

According to one further embodiment the location of the gaze point in an arbitrary scene image can be performed in a slightly different way. Assuming that the gaze point at a first scene image has already been determined, then for a second scene image taken form a different position the gaze point mapping procedure as described in European patent application no. 11158922.2 can be used.

It should be noted that the 3D Structure Detector, Head Tracker, and position detecting device can all be implemented by a camera combined with a suitable method to extract the necessary information out of the images. In such an embodiment the eye tracker only needs to be combined with a scene camera and a device (such as a computer which is suitably programmed) that carries out the extraction methods to extract the data such as the 3D structure, the camera position and the head position.

According to one embodiment, instead of a head-mounted eye tracker a remote eye tracker may be used. If this remote eye tracker is located at a fixed position and has a fixed coordinate system, its coordinate system may be used as reference coordinate system or it at least has a known spatial relationship with the reference coordinate system of the 3D structure detector. If the remote eye tracker is capable of directly obtaining the gaze direction in its own time invariant coordinate system, then no further "separate" head tracker is needed, the eye tracker then—by the determination of the eye position and orientation which is performed also by such an eye tracker—simultaneously is also an implementation of a head tracking unit.

According to one embodiment the scene camera can move relative to the eyetracker. Its position may be determined by an object tracker and then the gaze point may be projected onto the scene image as described before regardless of its position.

What is claimed is:

1. A method comprising:
    at a computing device including an eye tracker;
    determining, by the computing device, a gaze endpoint of a subject in 3D space based on a vergence of two eyes using gaze directions of the two eyes in a 3D reference coordinate system detected by the eye tracker;
    determining, by the computing device, a plurality of respective distances between the gaze endpoint and a plurality of representative points as a plurality of object representations representing a plurality of locations of a plurality of objects in the 3D space;
    determining by the computing device, which object representation of the plurality of object representations the subject is gazing at based on the plurality of distances between the gaze endpoint and the plurality of the object representations; and
    identifying, by the computing device, which object among the plurality of objects the subject is gazing at based on the determined object representation.

2. The method of claim 1,
    wherein via coordinates in the 3D reference coordinate system, the plurality of objects in the 3D space is represented.

3. The method of claim 1, wherein the gaze endpoint lies in an empty space where no object of the plurality of objects is located.

4. The method of claim 3, wherein determining which object representation of the plurality of object representations the subject is gazing at based on the plurality of distances between the gaze endpoint and the plurality of the object representations includes:
    choosing a respective object representation from the plurality of object representations that is most close to the gaze endpoint.

5. The method of claim 1, wherein the plurality of object representations includes a single point representing a location of a respective object in the 3D space.

6. The method of claim 5, wherein the single point is off center of the respective object.

7. The method of claim 1, wherein the plurality of object representations includes a respective object representation that includes an extension from a center point of a respective object.

8. A non-transitory computer-readable medium having programs which, when executed by a computing device with an eye tracker, cause the computing device to:
    determine a gaze endpoint of a subject in 3D space based on a vergence of two eyes using gaze directions of the two eyes in a 3D reference coordinate system detected by the eye tracker;
    determine a plurality of respective distances between the gaze endpoint and a plural of representative points as a plurality of object representations representing a plurality of locations of a plurality of objects in the 3D space;
    determine which object representation of the plurality of object representations the subject is gazing at based on the plurality of distances between the gaze endpoint and the plurality of the object representations; and
    identify which object among the plurality of objects the subject is gazing at based on the determined object representation.

9. The non-transitory computer-readable medium of claim 8,
    wherein via coordinates in the 3D reference coordinate system, the plurality of objects in the 3D space is represented.

10. The non-transitory computer-readable medium of claim 8, wherein the gaze endpoint lies in an empty space where no object of the plurality of objects is located.

11. The non-transitory computer-readable medium of claim 8, wherein determining which object representation of the plurality of object representations the subject is gazing at based on the plurality of distances between the gaze endpoint and the plurality of the object representations includes:
    choosing a respective object representation from the plurality of object representations that is most close to the gaze endpoint.

12. The non-transitory computer-readable medium of claim 8, wherein the plurality of object representations includes a single point representing a location of a respective object in the 3D space.

13. The non-transitory computer-readable medium of claim 12, wherein the single point is off center of the respective object.

14. The non-transitory computer-readable medium of claim 8, wherein the plurality of object representations includes a respective object representation that includes an extension from a center point of a respective object.

15. An electronic device comprising:
    an eye tracker to track gaze directions of two eyes of a subject;
    a memory to store a plurality of object representations of a plurality of objects in 3D space; and
    one or more processors to:
        determine a gaze endpoint of the subject in the 3D space based on a vergence of the two eyes using the gaze directions of the two eyes in a 3D reference coordinate system detected by the eye tracker;
        determine a plurality of respective distances between the gaze endpoint and a plurality of representative points as a plurality of object representations representing a plurality, of locations of a plurality of objects in the 3D space;
        determine which object representation of the plurality of object representations the subject is gazing at based on the plurality of distances between the gaze endpoint and the plurality of the object representations; and identify which object among the plurality of objects the subject is gazing at based on the determined object representation.

16. The electronic device of claim 15,
the plurality of objects in the 3D space is represented via coordinates in the 3D reference coordinate system.

17. The electronic device of claim 15, wherein the gaze endpoint lies in an empty space where no object of the plurality of objects is located.

18. The electronic device of claim 15, wherein determining which object representation of the plurality of object representations the subject is gazing at based on the plurality of distances between the gaze endpoint and the plurality of the object representations includes:

choosing a respective object representation from the plurality of object representations that is most close to the gaze endpoint.

19. The electronic device of claim 15, wherein the plurality of object representations includes a single point representing a location of a respective object in the 3D space.

20. The electronic device of claim 19, wherein the single point is off center of the respective object.

* * * * *